(12) United States Patent
Parvulescu et al.

(10) Patent No.: US 10,774,057 B2
(45) Date of Patent: Sep. 15, 2020

(54) PROCESS FOR PREPARING ETHENE OXIDE

(71) Applicant: BASF SE, Ludwigshafen am Rhein (DE)

(72) Inventors: Andrei-Nicolae Parvulescu, Ludwigshafen (DE); Ulrich Mueller, Ludwigshafen (DE); Joaquim Henrique Teles, Ludwigshafen (DE); Dominic Riedel, Ludwigshafen (DE); Markus Weber, Ludwigshafen (DE); Yan Li, Shanghai (CN)

(73) Assignee: BASF SE, Ludwigshafen am Rhein (DE)

(*) Notice: Subject to any disclaimer, the term of this patent is extended or adjusted under 35 U.S.C. 154(b) by 0 days.

(21) Appl. No.: 16/310,645

(22) PCT Filed: Jul. 12, 2017

(86) PCT No.: PCT/EP2017/067576
§ 371 (c)(1),
(2) Date: Dec. 17, 2018

(87) PCT Pub. No.: WO2018/011280
PCT Pub. Date: Jan. 18, 2018

(65) Prior Publication Data
US 2019/0330171 A1    Oct. 31, 2019

(30) Foreign Application Priority Data

Jul. 13, 2016 (EP) ..................... 16179235

(51) Int. Cl.
*C07D 301/12* (2006.01)
*B01J 29/70* (2006.01)
(52) U.S. Cl.
CPC ........ *C07D 301/12* (2013.01); *B01J 29/7088* (2013.01); *B01J 2229/186* (2013.01)
(58) Field of Classification Search
CPC .................................................. C07D 301/12

USPC ......................................................... 549/531
See application file for complete search history.

(56) References Cited

U.S. PATENT DOCUMENTS

| 2007/0027347 A1 | 2/2007 | Miller et al. |
| 2007/0099299 A1 | 5/2007 | Simon et al. |
| 2007/0276166 A1 | 11/2007 | Miller et al. |
| 2016/0176835 A1 | 6/2016 | Riedel et al. |

FOREIGN PATENT DOCUMENTS

| EP | 1 122 249 A1 | 8/2001 |
| WO | WO 2007/018684 A1 | 2/2007 |
| WO | WO 2013/117536 A2 | 8/2013 |
| WO | WO 2015/010990 A1 | 1/2015 |

OTHER PUBLICATIONS

International Search Report dated Aug. 4, 2017 in PCT/EP2017/067576 filed Jul. 12, 2017.
International Preliminary Report on Patentability and Written Opinion dated Jan. 24, 2019 in PCT/EP2017/067576.
Frank Stallmach, et al., "Spin Echo NMR Diffusion Studies", Annual Reports on NMR Spectroscopy, vol. 61, 2007, pp. 51-131.
Xinqing Lu, et al., "Selective synthesis of ethylene oxide through liquid-phase epoxidation of ethylene with titanosilicate/$H_2O_2$ catalytic systems", Applied Catalysis A: General, vol. 515, 2016, pp. 51-59.

*Primary Examiner* — Taofiq A Solola
(74) *Attorney, Agent, or Firm* — Oblon, McClelland, Maier & Neustadt, L.L.P.

(57) ABSTRACT

A process for preparing ethene oxide comprising providing a liquid feed stream comprising ethene, hydrogen peroxide, and a solvent; passing the liquid feed stream into an epoxidation zone comprising a catalyst comprising a titanium zeolite comprising zinc and having framework type MWW, and subjecting the liquid feed stream to epoxidation reaction conditions in the epoxidation zone, obtaining a reaction mixture comprising ethene oxide, water, and the solvent; removing an effluent stream from the epoxidation zone, the effluent stream comprising ethene oxide, water and the solvent.

15 Claims, 3 Drawing Sheets

PROCESS FOR PREPARING ETHENE OXIDE

The present invention is directed to a liquid phase process for preparing ethene oxide wherein ethene is epoxidized by hydrogen peroxide in the presence of a titanium zeolite comprising zinc and having framework type MWW in a solvent.

EO is an important intermediate in the chemical industry. It is currently prepared by a gas phase process by reacting ethene with oxygen. Due to the typical low conversion of ethylene of less than 20% per reactor pass and the need of a ballast gas, usually methane, employed in order to remove the reaction heat, a large gas loop is required which finally results in large investment and high energy costs necessary, for example, for compressors and the like. Yet further, around 15% of ethene are generally lost in the form of $CO_2$.

X. Lu et al. disclose the synthesis of ethylene oxide in a liquid phase process using hydrogen peroxide as epoxidation agent. As catalytically active materials, titanosilicates are described, namely Ti-MWW, TS-1, Ti-MOR and Ti-Beta. The system Ti-MWW/hydrogen peroxide/acetonitrile was identified as the best reaction system. In this article, the epoxidation reactions were carried out in a batch reactor (autoclave reactor) for a very limited reaction time of only 1.5 hours. Usually, such experiments provide only very limited significance for industrial-scale processes which typically aim at very long times on stream with a catalyst allowing for very high selectivities and, at the same time, conversion rates over the complete time on stream. It is noted that even for the best reaction system according to X. Lu et al., a hydrogen peroxide conversion of only 54.4% was achieved which is not acceptable for an industrial-scale process.

Therefore, it was a problem underlying the present invention to provide a process for preparing ethene oxide by epoxidizing ethene with hydrogen peroxide in the presence of a catalyst, which process exhibits high hydrogen peroxide conversion and ethene oxide selectivity over long reaction periods, thus rendering the process suitable as an industrial-scale process.

According to the present invention, it was found that this problem can be solved if the epoxidation is carried out in the presence if an epoxidation catalyst which comprises a titanium zeolite comprising zinc and having framework type MWW.

Thus, the present invention relates to a process for preparing ethene oxide, comprising
(i) providing a liquid feed stream comprising ethene, hydrogen peroxide, and a solvent;
(ii) passing the liquid feed stream provided in (i) into an epoxidation zone comprising a catalyst comprising a titanium zeolite comprising zinc and having framework type MWW, and subjecting the liquid feed stream to epoxidation reaction conditions in the epoxidation zone, obtaining a reaction mixture comprising ethene oxide, water, and the solvent;
(iii) removing an effluent stream from the epoxidation zone, the effluent stream comprising ethene oxide, water, and the solvent.

Preferably, the present invention relates to the process as defined above, being a continuous process. More preferably, the present invention relates to the process as defined above, being a process for continuously preparing ethene oxide, the process comprising
(i) continuously providing a liquid feed stream comprising ethene, hydrogen peroxide, and a solvent;
(ii) continuously passing the liquid feed stream provided in (i) into an epoxidation zone comprising a catalyst comprising a titanium zeolite comprising zinc and having framework type MWW, and subjecting the liquid feed stream to epoxidation reaction conditions in the epoxidation zone, obtaining a reaction mixture comprising ethene oxide, water, and the solvent;
(iii) continuously removing an effluent stream from the epoxidation zone, the effluent stream comprising ethene oxide, water, and the solvent.

Liquid Feed Stream Provided in (i)

Preferably, in the liquid feed stream provided in (i), the molar ratio of ethene relative to hydrogen peroxide is in the range of from 1:1 to 5:1, more preferably in the range of from 1:1 to 4:1, more preferably in the range of from 1:1 to 3:1, more preferably in the range of from 1:1 to 2:1, more preferably in the range of from 1:1 to 1.5:1.

Preferably, the liquid feed stream provided in (i) comprises the ethene in an amount in the range of from 5 to 30 weight-%, more preferably in the range of from 5.5 to 25 weight-%, more preferably in the range of from 6 to 20 weight-%, more preferably in the range of from 6.5 to 17.5 weight-%, more preferably in the range of from 7 to 15 weight-%, based on the total weight of the liquid feed stream.

Regarding to solvent comprised in the liquid feed stream according to (i), it is preferred that it comprises one or more organic solvents. More preferably, the solvent comprises, more preferably is, one or more of tert-butanol, propylene carbonate, methylacetate, and acetonitrile. More preferably, the solvent comprises acetonitrile. More preferably, the solvent is acetonitrile.

Preferably, the liquid feed stream provided in (i) comprises the solvent in an amount in the range of from 60 to 85 weight-%, more preferably in the range of from 61 to 84 weight-%, more preferably in the range of from 62 to 83 weight-%, more preferably in the range of from 63 to 82 weight-%, more preferably in the range of from 64 to 81 weight-%, more preferably in the range of from 65 to 80 weight-%, based on the total weight of the liquid feed stream. Preferred ranges can be from 65 to 70 weight-% or from 70 to 75 weight-% or from 75 to 80 weight-%.

Preferably, the liquid feed stream provided in (i) further comprises water. It is conceivable that at least part of the water is introduced as solvent for the hydrogen peroxide. The molar ratio of water relative to the solvent is, for example, at most 1:4, such as in the range of from 1:50 to 1:4 or in the range of from 1:15 to 1:4.1 or in the range of from 1:10 to 1:4.2.

Further, it is possible that the liquid feed stream provided in (i) further comprises one or more alkenes in addition to ethene wherein the one or more alkenes comprised in the liquid feed stream in addition to ethene preferably comprise propene. Preferably, the molar ratio of ethene relative to the sum of the one or more further alkenes is in the range of from 100:1.0 to 100:0.1.

Further, it is possible that the liquid feed stream provided in (i) further comprises one or more alkanes wherein the one or more alkanes preferably comprise one or more of methane and ethane. Preferably, the molar ratio of ethene relative to the sum of the one or more alkanes is in the range of from 100:2.0 to 100:0.1.

Preferably, at least 95 weight-%, more preferably at least 96 weight-%, more preferably at least 97 weight-%, more preferably at least 98 weight-%, more preferably at least 99 weight-% of the liquid feed stream provided in (i) consist of ethene, hydrogen peroxide, the solvent, and water.

Preferably, the liquid feed stream provided in (i) further comprises a dissolved salt, preferably a dissolved potassium salt. Regarding the chemical nature of the at least one potassium salt is concerned, no specific restrictions exist. Preferably, the potassium salt is one or more of an inorganic potassium salt and an organic potassium salt. Preferred inorganic potassium salts include, but are not restricted to, potassium halides such as potassium chloride or potassium bromide, potassium nitrate, potassium sulfate, potassium hydrogen sulfate, potassium hydroxide, potassium perchlorate, potassium salts comprising phosphorus such as potassium dihydrogen phosphate or dipotassium hydrogen phosphate or potassium phosphate or potassium pyrophosphates such as monobasic potassium pyrophosphate or dibasic potassium pyrophosphate or tribasic potassium pyrophosphate or tetrabasic potassium pyrophosphate, or potassium etidronates such as monobasic potassium etidronate or dibasic potassium etidronate or tribasic potassium etidronate or tetrabasic potassium etidronate, potassium cyanate, potassium oxides such as potassium oxide ($K_2O$) or potassium superoxide ($KO_2$) or potassium peroxide ($K_2O_2$). More preferably, the inorganic potassium salt is one or more of potassium hydroxide, a potassium halide, potassium nitrate, potassium sulfate, potassium hydrogen sulfate, potassium perchlorate, and a potassium salt of a phosphorus oxyacid. Said potassium salt of a phosphorus oxyacid preferably has the formula $K_{nx}H_{2+n(1-x)}P_nO_{3n+1}$, wherein n is an integer in the range of from 1 to 10, preferably in the range of from 1 to 5, more preferably in the range of from 1 to 3, and wherein x is in the range of from 0.6 to 1.4, preferably in the range of from 0.7 to 1.3, more preferably in the range of from 0.8 to 1.2, wherein more preferably, n is 1 and x is in the range of from 0.95 to 1.05.

Preferably, the organic potassium salt is one or more of aliphatic saturated monocarboxylic acids preferably having 1, 2, 3, 4, 5 or 6 carbon atoms, potassium carbonate, and potassium hydrogen carbonate, preferably one or more of potassium formate and potassium acetate. More preferably, the organic potassium salt comprises, preferably is, potassium formate.

Preferably, in the liquid feed stream provided in (i), the molar ratio of the dissolved salt, preferably the dissolved potassium salt, relative to the hydrogen peroxide is in the range of from $25\times10^{-6}$:1 to $500\times10^{-6}$:1, preferably in the range of from $50\times10^{-6}$:1 to $250\times10^{-6}$:1, more preferably in the range of from $100\times10^{-6}$:1 to $150\times10^{-6}$:1.

Therefore, it is preferred that at least 95 weight-%, more preferably at least 96 weight-%, more preferably at least 97 weight-%, more preferably at least 98 weight-%, more preferably at least 99 weight-% of the liquid feed stream provided in (i) consist of ethene, hydrogen peroxide, the solvent, water, and the dissolved salt, preferably the dissolved potassium salt.

Preferably, the liquid feed stream provided in (i) is passed as the sole feed stream into the epoxidation zone according to (ii).

It is conceivable that liquid feed stream provided in (i) is free of ammonium dihydrogen phosphate, such as free of ammonium phosphate, ammonium hydrogen phosphate and ammonium dihydrogen phosphate, preferably free of ammonium carbonate, ammonium hydrogen carbonate, ammonium dihydrogen phosphate, ammonium hydrogen phosphate, ammonium phosphate, ammonium hydrogen pyrophosphate, ammonium pyrophosphate, ammonium chloride, ammonium nitrate, and ammonium acetate, more preferably free of an ammonium salt. The term "free of" as used in this context of the present invention relates to a concentration of a respective compound of at most 2 weight-ppm, preferably at most 1 weight-ppm, based on the total weight of the liquid feed stream. It is further conceivable that the liquid feed stream provided in (i) contains sodium in a molar ratio of sodium relative to hydrogen peroxide in the range of from $1*10^{-6}$:1 to $250*10^{-6}$:1, preferably in the range of from $5*10^{-6}$:1 to $50*10^{-6}$:1. It is further conceivable that the liquid feed stream provided in (i) does not comprise dissolved sodium dihydrogen phosphate ($NaH_2PO_4$), preferably neither dissolved sodium dihydrogen phosphate nor dissolved disodium hydrogen phosphate ($Na_2HPO_4$), more preferably neither dissolved sodium dihydrogen phosphate nor dissolved disodium hydrogen phosphate nor dissolved sodium phosphate ($Na_3PO_4$).

Preferably, the liquid feed stream provided in (i) is under a pressure and a temperature at which the liquid feed stream is a liquid stream consisting of one or more liquid phases, preferably one or two liquid phases. Preferably, the liquid feed stream provided in (i) is under a pressure in the range of from 18 to 60 bar(abs), more preferably in the range of from 30 to 60 bar(abs), more preferably in the range of from 35 to 55 bar(abs), more preferably in the range of from 40 to 50 bar(abs). Preferably, the liquid feed stream provided in (i) has a temperature in the range of from 20 to 60° C., more preferably in the range of from 25 to 50° C., more preferably in the range of from 30 to 45° C. More preferably, the liquid feed stream provided in (i) is under a pressure in the range of from 30 to 60 bar(abs), more preferably in the range of from 35 to 55 bar(abs), more preferably in the range of from 40 to 50 bar(abs), and has a temperature in the range of from 20 to 60° C., more preferably in the range of from 25 to 50° C., more preferably in the range of from 30 to 45° C. It may be conceivable that the liquid feed stream provided in (i) is under a pressure and a temperature at which, in addition to the one or more liquid phases, a gas phase exists wherein, for example, a small portion of the ethene may be present as a gas.

Generally, the liquid feed stream can be provided in (i) according to any conceivable method, such as by combining at least four individual streams wherein a first stream comprises hydrogen peroxide, a second stream comprises ethene, a third stream comprises the solvent and optionally water, and a fourth stream comprises the salt, preferably the potassium salt, in an amount so that the salt is dissolved in the liquid feed stream provided in (i).

The stream comprising hydrogen peroxide can be prepared according to every conceivable method. It is conceivable to obtain the stream comprising hydrogen peroxide by converting sulphuric acid into peroxodisulphuric acid by anodic oxidation with simultaneous evolution of hydrogen at the cathode. Hydrolysis of the peroxodisulphuric acid then leads via peroxomonosulphuric acid to hydrogen peroxide and sulphuric acid which is thus obtained back. The preparation of hydrogen peroxide from the elements is also conceivable. Depending on the specific preparation method, the stream comprising hydrogen peroxide can be, for example, an aqueous or an aqueous/methanolic hydrogen peroxide stream, preferably an aqueous hydrogen peroxide stream. In case an aqueous hydrogen peroxide feed is employed, the content of the stream with respect to hydrogen peroxide is usually in the range of from 3 to 85 weight-%, preferably from 25 to 75 weight-%, more preferably from 30 to 50 weight-%, such as from 30 to 40 weight-% or from 35 to 45 weight-% of from 40 to 50 weight-%. Preferably, at least 25 weight-%, more preferably at least 30 weight-%, more preferably at least 35 weight-% of the stream comprising hydrogen peroxide consist of water and hydrogen peroxide. Preferred ranges are from 30 to 80 weight % or from 35 to 75 weight-% or from 40 to 70 weight-%. It may be preferred to employ a stream comprising hydrogen peroxide which is obtained as crude hydrogen peroxide solution by extraction of a mixture which results from a process known as anthraquinone process by means of which virtually the entire world production of hydrogen peroxide is produced (see, e.g., Ullmann's Encyclopedia of Industrial Chemistry, 5$^{th}$ edition, volume A 13 (1989) pages 443-466) wherein a solution of an anthraquinone is used containing an alkyl group preferably having of from 2 to 10 carbon atoms, more preferably at least 5 carbon atoms such as 5 carbon atoms or 6 carbon atoms and where the solvent used usually consists of a mixture of two different solvents. This solution of the anthraquinone is usually referred to as the working solution. In this process, the hydrogen peroxide formed in the course of the anthraquinone process is generally separated by extraction from the respective working solution after a hydrogenation/re-oxidation cycle. Said extraction can be performed preferably with essentially pure water, and the crude aqueous hydrogen peroxide solution is obtained. While it is generally possible to further purify the thus obtained crude aqueous hydrogen peroxide solution by distillation, it is preferred, according to the present invention, to use such crude aqueous hydrogen peroxide solution which has not been subjected to purification by distillation. Further, it is generally possible to subject the crude aqueous hydrogen peroxide solution to a further extraction stage wherein a suitable extracting agent, preferably an organic solvent is used. More preferably, the organic solvent used for this further extraction stage is the same solvent which is used in the anthraquinone process. Preferably the extraction is performed using just one of the solvents in the working solution and most preferably using just the most nonpolar solvent of the working solution. In case the crude aqueous hydrogen peroxide solution is subjected to such further extraction stage, a so-called crude washed hydrogen peroxide solution is obtained. According to a preferred embodiment of the present invention, the crude washed hydrogen peroxide solution is used as hydrogen peroxide feed. The production of a crude solution is described, for example, in European patent application EP 1 122 249 A1. As to the term "essentially pure water", reference is made to paragraph 10, page 3 of EP 1 122 249 A1 which is incorporated by reference. In order to provide a sufficient stability of the hydrogen peroxide during extraction with water, preferably essentially pure water, suitable stabilizing agents are usually added to the water, preferably the essentially pure water used. In particular, strong inorganic acids and/or chelating agents are to be mentioned. Small amounts of nitrates and/or phosphates and pyrophosphates, respectively, may be added as stabilizing agents, either as acids or as sodium salts. These stabilizing agents are usually added in amounts so that the crude aqueous hydrogen peroxide solution contains from 50 to 400 weight-ppm sodium cations, from 100 to 700 weight-ppm phosphorus calculated as phosphate ($PO_4^{3-}$), and from 50 to 400 weight-ppm nitrate anions, in each case calculated with respect to hydrogen peroxide contained in the crude aqueous hydrogen peroxide solution. Preferred ranges are, for example, from 50 to 200 weight-ppm or from 50 to 100 weight-ppm of sodium cations, from 100 to 500 weight-ppm or from 100 to 300 weight-ppm of phosphorus, and 50 to 200 weight-ppm or 50 to 100 weight-ppm of nitrate. Further, it is conceivable that other stabilizing agents such as stannites like sodium stannite ($Na_2SnO_2$) and/or organic phosphonic acids, in particular organic diphosphonic acids like etidronic acid are used. Preferably, the aqueous hydrogen peroxide stream comprises sodium with a molar ratio of sodium relative to hydrogen peroxide in the range of from $1\times10^{-6}$:1 to $250\times10^{-6}$:1, more preferably from $5\times10^{-6}$:1 to $50\times10^{-6}$:1.

Epoxidation Zone in (ii)

Preferably, in the epoxidation zone according to (ii), the reaction mixture is liquid under the epoxidation conditions. More preferably, in the epoxidation zone according to (ii), the reaction mixture consists of one single liquid phase under the epoxidation conditions.

According to (ii), the liquid feed stream provided in (i) is passed into an epoxidation zone. Generally, there are no specific restrictions regarding the design of the epoxidation zone provided that it is suitable for carrying out a continuous epoxidation reaction. Preferably, the epoxidation zone according to (ii) comprises one or more epoxidation subzone wherein a given epoxidation subzone preferably consist of one or more epoxidation reactors wherein, with regard to the design of the one or more epoxidation reactors, no specific restrictions exist provided that the reactors are suitable for carrying out a continuous epoxidation reaction.

Preferably, the epoxidation zone according to (ii) comprises a first epoxidation subzone consisting of one or more epoxidation reactors A. The term "first epoxidation subzone" as used in this context of the present invention relates to the epoxidation subzone into which the liquid feed stream provided in (i) is passed, wherein the epoxidation zone of (ii) may comprise further epoxidation subzones which are arranged downstream of the first epoxidation subzone. If the first epoxidation subzone consisting of two or more epoxidation reactors A, it is preferred that the two or more epoxidation reactors A are arranged in parallel. In this case, it is preferred that in (ii), the liquid feed stream provided in (i) is passed into at least one of the epoxidation reactors A. It is possible, for example, that, while the liquid feed stream provided in (i) is passed into at least one of the epoxidation reactors A, at least one of the reactors A is taken out of operation, for example for maintenance purposes and/or for regenerating the catalyst comprised in the at least one of the reactors A. If the first epoxidation subzone comprises two or more epoxidation reactors A, the reactors in operation are operated essentially identically so that in every epoxidation reactor A in operation, a given epoxidation condition is in the same range.

According to a preferred embodiment of the present invention, the epoxidation zone according to (ii) consists of the first epoxidation subzone.

Preferably, the epoxidation conditions according to (ii) comprise an epoxidation temperature in the first epoxidation subzone in the range of from 20 to 60° C., more preferably in the range of from 25 to 50° C., more preferably in the range of from 30 to 45° C., wherein said epoxidation temperature is defined as the temperature of a heat transfer medium used for adjusting the temperature of the reaction mixture in the first epoxidation reaction subzone, preferably by passing the heat transfer medium through a jacket of the one or more epoxidation reactors A, wherein said epoxidation temperature is preferably the temperature of the heat transfer medium prior to adjusting the temperature of the reaction mixture, more preferably the temperature of the heat transfer medium at the entrance of the jacket of the one or more epoxidation reactors A.

Preferably, the epoxidation conditions according to (ii) comprise a first epoxidation reaction pressure in the range of from 18 to 60 bar(abs), more preferably in the range of from 30 to 60 bar(abs), preferably in the range of from 35 to 55 bar(abs), more preferably in the range of from 40 to 50 bar(abs), wherein the first epoxidation reaction pressure is defined as the absolute pressure at the exit of the first epoxidation subzone.

Preferably, the epoxidation conditions according to (ii) comprise a catalyst loading in the first epoxidation subzone in the range of from 0.05 to 1.25 $h^{-1}$, more preferably in the range of from 0.1 to 1 $h^{-1}$, more preferably in the range of from 0.2 to 0.7 $h^{-1}$, wherein the catalyst loading is defined as the ratio of the mass flow rate in kg/h of hydrogen peroxide contained in liquid feed stream provided in (i) and passed into (ii) relative to the amount in kg of catalyst comprising a titanium zeolite having framework type MWW comprised in the first epoxidation subzone according to (ii). If the first epoxidation subzone comprises two or more epoxidation reactors A, the catalyst loading in the first epoxidation subzone relates to the catalyst loading in a given reactor A in operation of first epoxidation subzone.

According to a second preferred embodiment of the present invention, the epoxidation zone according to (ii) additionally comprises a second epoxidation subzone consisting of one or more epoxidation reactors B wherein, if the second epoxidation subzone comprises two or more epoxidation reactors B, the two or more epoxidation reactors B are arranged in parallel, wherein the second epoxidation subzone is arranged downstream of the first epoxidation subzone. In this case, it is preferred that in (ii), the effluent stream obtained from the first epoxidation subzone, optionally after a suitable intermediate treatment, is passed into at least one of the epoxidation reactors B. It is possible, for example, that, while the effluent stream obtained from the first epoxidation subzone, optionally after a suitable intermediate treatment, is passed into at least one of the epoxidation reactors B, at least one of the reactors B is taken out of operation, for example for maintenance purposes and/or for regenerating the catalyst comprised in the at least one of the reactors B. If the second epoxidation subzone comprises two or more epoxidation reactors B, the reactors in operation are operated essentially identically so that in every epoxidation reactor B in operation, a given epoxidation condition is in the same range in every reactor. Generally, it is conceivable that in addition to the first epoxidation subzone and the second epoxidation subzone, the epoxidation zone according to (ii) comprises at least one further epoxidation subzone arranged downstream of the second epoxidation subzone.

Preferably, according to the second preferred embodiment of the present invention, the epoxidation zone according to (ii) consists of the first epoxidation subzone and the second epoxidation subzone.

Preferably, the epoxidation conditions according to (ii) comprise a second epoxidation reaction pressure in the range of from 18 to 60 bar(abs), preferably in the range of from 30 to 60 bar (abs), preferably in the range of from 35 to 55 bar(abs), more preferably in the range of from 40 to 50 bar(abs), wherein the first epoxidation reaction pressure is defined as the absolute pressure at the exit of the second epoxidation subzone.

Preferably, the epoxidation conditions according to (ii) comprise a catalyst loading in the second epoxidation subzone in the range of from 0.001 to 0.5 $h^{-1}$, preferably in the range of from 0.005 to 0.3 $h^{-1}$, more preferably in the range of from 0.01 to 0.2 $h^{-1}$, wherein the catalyst loading is defined as the ratio of the mass flow rate in kg/h of hydrogen peroxide contained in the feed stream passed into the second epoxidation subzone relative to the amount in kg of catalyst comprising a titanium zeolite comprising zinc and having framework type MWW comprised in the second epoxidation subzone according to (ii).

Preferably, the temperature of the reaction mixture in the second epoxidation reaction subzone is not adjusted by passing a heat transfer medium through a jacket of the one or more epoxidation reactors B. More preferably, the second epoxidation subzone is an essentially adiabatic epoxidation subzone. More preferably, the second epoxidation subzone is an adiabatic epoxidation subzone.

The effluent stream obtained from the first epoxidation subzone, prior to being passed in to the second epoxidation subzone, may be subjected to a suitable intermediate treatment. It is preferred that during such intermediate treatment, the chemical composition of the stream is not changed. More preferably, the intermediate treatment comprises a heat exchange according to which, more preferably, the temperature of the effluent stream obtained from the first epoxidation subzone is decreased before the stream is passed into the second epoxidation subzone. The energy withdrawn from the stream can be used at one or more suitable stages of the overall epoxidation process, for example for increasing the temperature of a suitable process stream.

Catalyst in (ii)

Preferably, the catalyst comprising the titanium zeolite comprising zinc and having framework type MWW is present in the epoxidation zone as a molding, preferably as fluidized-bed catalyst or a fixed-bed catalyst, more preferably as a fixed-bed catalyst.

Preferably, the catalyst according to (ii) is characterized by a specific tortuosity parameter reflecting the diffusion characteristics of fluids through the porous structure of the molding. Preferably, the tortuosity of parameter of the catalyst according to (ii) relative to water is at most 4, more preferably less than 4, more preferably at most 3.5, more preferably at most 3. More preferably, the tortuosity of parameter of the catalyst according to (ii) relative to water is in the range of from 0 to 4, more preferably in the range of from from 0 to less than 4, more preferably in the range of from 0 to 3.5, more preferably in the range of 0 to 3. The term "tortuosity parameter" as used herein refers to the tortuosity characteristic of the inventive materials at a temperature of 298.15 K and preferably as defined in US 2007/0099299 A1, and more preferably as defined Reference Example 1.1 hereinbelow.

Preferably, the titanium zeolite comprising zinc and having framework type MWW comprised in the catalyst according to (ii) contains titanium, calculated as elemental titanium, in an amount in the range of from 0.1 to 5 weight-%, more preferably in the range of from 0.5 to 4 weight-%, more preferably in the range of from 1 to 3 weight-%, such as from 1 to 2 weight-% or from 1.5 to 2.5 weight-% or from 2 to 3 weight-%, based on the total weight of the titanium zeolite comprising zinc and having framework type MWW.

Preferably, the titanium zeolite comprising zinc and having framework type MWW comprised in the catalyst according to (ii) contains zinc, calculated as elemental zinc, in an amount in the range of from 0.1 to 5 weight-%, more preferably in the range of from 0.5 to 4 weight-%, more preferably in the range of from 1 to 3 weight-%, such as from 1 to 2 weight-% or from 1.5 to 2.5 weight-% or from 2 to 3 weight-%, based on the total weight of the titanium zeolite comprising zinc and having framework type MWW.

Preferably, at least 98 weight-%, more preferably at least 98.5 weight-%, more preferably at least 99 weight-%, more preferably at least 99.5 weight-%, more preferably at least 99.9 weight-% of the titanium zeolite comprising zinc and having framework type MWW consist of Zn, Ti, Si, O, and H.

The catalyst comprising the titanium zeolite comprising zinc and having framework type MWW can be employed in every conceivable, including a powder, a micropowder, such as a spraypowder, as a molding comprising a powder, or as a molding comprising a micropowder, such as a spray-powder. Preferably, the catalyst comprising the titanium zeolite comprising zinc and having framework type MWW is employed as a molding comprising a powder or a micropowder, such as a spray-powder, more preferably as a molding comprising a micropowder, such as a spray-powder. Regarding a preferred micropowder, reference is made to the micropowder characterized by the respective micropowder embodiments 1 to 14 hereinbelow. Regarding a preferred molding, reference is made to the molding characterized by the respective molding embodiments 1 to 8 hereinbelow. Preferably, the catalyst comprising the titanium zeolite comprising zinc and having framework type MWW is in the form of a molding, comprising the titanium zeolite having framework type MWW and a binder, preferably a silica binder. Preferably, the catalyst comprises the titanium zeolite comprising zinc and having framework type MWW preferably in an amount in the range of from 70 to 80 weight-%, based on the total weight of the catalyst, and the silica binder preferably in an amount of from 30 to 20 weight-%, based on the total weight of the catalyst, wherein preferably at least 95 weight-%, more preferably at least 98 weight-%, more preferably at least 99 weight-% of the catalyst consist of the titanium zeolite comprising zinc and having framework type MWW and the binder.

Said catalyst used according to step (ii) of the present invention, being present in the form of a micropowder comprising the titanium zeolite comprising zinc and having framework type MWW, is preferably characterized by the following features and embodiments, including the combinations of embodiments according to the given dependencies:

1. A micropowder, the particles of which having a Dv10 value of at least 2 micrometer, said micropowder comprising mesopores having an average pore diameter (4V/A) in the range of from 2 to 50 nm as determined by Hg porosimetry according to DIN 66133, and comprising, based on the weight of the micropowder, at least 95 weight-% of the titanium zeolite comprising zinc and having framework type MWW. The Dv10 value is understood as being determined according to Reference Example 1.2 of the present invention.
2. The micropowder of embodiment 1, having a Dv10 value in the range of from 2 to 5.5 micrometer, preferably from 3 to 5.5 micrometer.
3. The micropowder of embodiment 1 or 2, having a Dv50 value in the range of from 7 to 25 micrometer and optionally a Dv90 value in the range of from 26 to 85 micrometer. The Dv50 and Dv90 values are understood as being determined according to Reference Example 1.2 of the present invention.
4. The micropowder of any of embodiments 1 to 3, wherein the mesopores have an average pore diameter (4V/A) in the range of from 10 to 50 nm, preferably of from 15 to 40 nm, more preferably of from 20 to 30 nm, as determined by Hg porosimetry according to DIN 66133.
5. The micropowder of any of embodiments 1 to 4, additionally comprising macropores having an average pore diameter (4V/A) in the range of from more than 50 nm, said macropores preferably having an average pore diameter in the range of from 0.05 to 3 micrometer, as determined by Hg porosimetry according to DIN 66133.
6. The micropowder of any of embodiments 1 to 5, wherein the micropores of the titanium zeolite comprising zinc and having framework type MWW have an average pore diameter in the range of from 1.0 to 1.2 nanometer as determined by nitrogen adsorption according to DIN 66135.
7. The micropowder of any of embodiments 1 to 6, comprising, based on the weight of the micropowder, at least 99 weight-%, preferably at least 99.7 weight-% of the titanium zeolite comprising zinc and having framework type MWW.
8. The micropowder of any of embodiments 1 to 7, wherein the titanium zeolite comprising zinc and having framework type MWW contains zinc in an amount of from 0.1 to 5 weight-%, preferably of from 1 to 3 weight-%, calculated as Zn and based on the weight of the titanium zeolite comprising zinc and having framework type MWW.
9. The micropowder of any of embodiments 1 to 8, wherein the titanium zeolite comprising zinc and having framework type MWW contains titanium in an amount of from 0.5 to 5 weight-%, preferably of from 1 to 3 weight-%, calculated as Ti and based on the weight of the titanium zeolite comprising zinc and having framework type MWW.
10. The micropowder of any of embodiments 1 to 9, having a crystallinity, as determined by X-ray diffraction (XRD) analysis, of at least (70+/−10)%, preferably of at least (80+/−10)%. The crystallinity is understood as being determined according to Reference Example 1.8 of the present invention.
11. The micropowder of any of embodiments 1 to 10, comprising, based on the total weight of the micropowder and calculated as element, less than 0.001 weight-%, preferably less than 0.0001 weight-% of a noble metal, preferably selected from the group consisting of gold, silver, platinum, palladium, iridium, ruthenium, osmium, and a mixture of two or more thereof, more preferably selected from the group consisting of gold, platinum, gold, and a mixture of two or more thereof.
12. The micropowder of any of embodiments 1 to 11, comprising, based on the total weight of the micropowder and calculated as element, less than 0.1 weight.-%, preferably less than 0.01 weight-% of boron.
13. The micropowder of any of embodiments 1 to 12, having a bulk density of in the range of from 80 to 500 g/ml.
14. The micropowder of any of embodiments 1 to 13, being a spray powder, preferably obtainable or obtained by spray-drying or by spin-flash drying or by microwave drying.

Further, said catalyst used according to step (ii) of the present invention being present in the form of a molding comprising the titanium zeolite comprising zinc and having framework type MWW, is preferably characterized by the following features and embodiments, including the combinations of embodiments according to the given dependencies:

1. A molding, comprising the titanium zeolite comprising zinc and having framework type, said molding preferably comprising a micropowder comprising, based on the weight of the micropowder, at least 95 weight-% of the titanium zeolite comprising zinc and having framework type MWW, said molding more preferably comprising the micropowder according to any of the micropowder embodiments 1 to 14 as described hereinabove, the molding preferably further comprising at least one binder, preferably a silica binder.
2. The molding of embodiment 1, comprising mesopores having an average pore diameter in the range of from 4 to 40 nm, preferably from 20 to 30 nm as determined by Hg porosimetry according to DIN 66133.

3. The molding of embodiment 1 or 2, having a crystallinity, as determined by XRD analysis, of at least (55+/−10) %, preferably in the range of from ((55 to 75)+/−10)%. The crystallinity is understood as being determined according to Reference Example 1.8 of the present invention.

4. The molding of any of embodiments 1 to 3, comprising the micropowder in an amount in the range of from 70 to 80 weight-% and the silica binder in an amount of from 30 to 20 weight-%, the micropowder together with the silica binder constituting at least 99 weight-% of the molding, wherein the molding has a concentration of silanol groups with respect to the total number of Si atoms of at most 6%, preferably at most 3%, as determined according to $^{29}$Si MAS NMR. The concentration of the silanol groups is understood as being determined according to Reference Example 1.3 of the present invention.

5. The molding of any of embodiments 1 to 4, being a strand having circular cross-section and a diameter in the range of from 1.5 to 1.7 mm and having a crush strength of at least 5 N, preferably in the range of from 5 to 30 N, more preferably in the range of from 12 to 20 N, the crush strength being determined by crush strength test machine Z2.5/TS1S according to the method as described in Reference Example 1.4 of the present invention.

6. The molding of any of embodiments 1 to 5, the $^{29}$Si-NMR spectrum of said molding comprising six peaks at the following position
peak 1 at −98+/−xppm,
peak 2 at −104+/−xppm,
peak 3 at −110+/−xppm,
peak 4 at −113+/−xppm,
peak 5 at −115+/−xppm,
peak 6 at −118+/−xppm,
with x in any of the peaks being 1.5, preferably 1.0, more preferably 0.5,
wherein Q which is defined as $$Q=100*\{[a_1+a_2]/[a_4+a_5+a_6]\}/a_3$$

is at most 2.5, preferably at most 1.6, preferably at most 1.4, with $[a_1+a_2]$ being the sum of the peak areas of peaks 1 and 2, and $[a_4+a_5+a_6]$ being the sum of the peak areas of peaks 4, 5, and 6, and $a_3$ being the peak area of peak 3. These $^{29}$Si-NMR characteristics are understood as being determined according the Reference Example 1.5 of the present invention.

7. The molding of any of embodiments 1 to 6, having a water uptake in the range of from 3 to 8 weight-%, preferably from 4 to 7 weight-%. The water uptake is understood as being determined according to Reference Example 1.6 of the present invention.

8. The molding of any of embodiments 1 to 7, the infrared spectrum of said molding comprising a band in the region of (3700-3750)+/−20 cm$^{-1}$ and a band in the region of (3670-3690)+/−20 cm$^{-1}$, wherein the intensity ratio of the band in the region of (3700-3750)+/−20 cm$^{-1}$ relative to the band in the region of (3670-3690)+/−20 cm$^{-1}$ is at most 1.5, preferably at most 1.4. These IR characteristics are understood as being determined according the Reference Example 1.7 of the present invention.

Conversions and Selectivities

Preferably, the epoxidation conditions according to (ii) comprise a hydrogen peroxide conversion in the range of from 85 to 100%, more preferably in the range of from 90 to 100%, more preferably in the range of from 95 to 100%, wherein the hydrogen peroxide conversion is defined as 100×(1−y) %, wherein y is the molar amount of hydrogen peroxide comprised in the effluent stream removed in (iii) relative to the molar amount of hydrogen peroxide comprised in the liquid feed stream provided in (i).

Preferably, the ethene oxide selectivity S(HP) of the epoxidation reaction in the epoxidation reaction zone according to (ii) is in the range of from 80 to 100%, more preferably in the range of from 85 to 100%, more preferably in the range of from 90 to 100%, wherein the ethene oxide selectivity S(HP) is defined as the molar amount of ethene oxide comprised in the effluent stream removed in (iii) relative to the molar amount of hydrogen peroxide comprised in the liquid feed stream provided in (i).

Preferably, the ethene oxide selectivity S(ET) of the epoxidation reaction in the epoxidation reaction zone according to (ii) is in the range of from 85 to 100%, more preferably in the range of from 90 to 100%, more preferably in the range of from 95 to 100%, wherein the ethene oxide selectivity S(ET) is defined as the molar amount of ethene oxide comprised in the effluent stream removed in (iii) relative to the molar amount of hydrogen peroxide comprised in the liquid feed stream provided in (i).

More preferably, the ethene oxide selectivity S(HP) of the epoxidation reaction in the epoxidation reaction zone according to (ii) is in the range of from 80 to 100%, more preferably in the range of from 85 to 100%, more preferably in the range of from 90 to 100%, and the ethene oxide selectivity S(ET) of the epoxidation reaction in the epoxidation reaction zone according to (ii) is in the range of from 85 to 100%, more preferably in the range of from 90 to 100%, more preferably in the range of from 95 to 100%.

More preferably, the epoxidation conditions according to (ii) comprise a hydrogen peroxide conversion in the range of from 85 to 100%, more preferably in the range of from 90 to 100%, more preferably in the range of from 95 to 100%, and the ethene oxide selectivity S(HP) of the epoxidation reaction in the epoxidation reaction zone according to (ii) is in the range of from 80 to 100%, more preferably in the range of from 85 to 100%, more preferably in the range of from 90 to 100%, and the ethene oxide selectivity S(ET) of the epoxidation reaction in the epoxidation reaction zone according to (ii) is in the range of from 85 to 100%, more preferably in the range of from 90 to 100%, more preferably in the range of from 95 to 100%.

Preferably, the effluent stream removed in (iii) comprises carbon dioxide in an amount in the range of from 100 to 1500 weight-ppm, more preferably in the range of from 150 to 1200 weight-ppm, more preferably in the range of from 200 to 1000 weight-ppm, based on the total weight of the effluent stream.

Downstream Stages/Work-Up

Generally, the effluent stream removed in (iii) comprises ethene oxide, water, and the solvent. Usually, the ethene will not be converted completey during the epoxidation according to (ii). Therefore, the effluent stream removed in (iii) preferably comprises ethene oxide, water, the solvent and ethene. Further, the effluent comprises a certain amount of oxygen preferably formed during the epoxidation according to (ii). Therefore, the effluent stream removed in (iii) preferably comprises ethene oxide, water, the solvent and oxygen. More preferably, the effluent stream removed in (iii) comprises ethene oxide, water, the solvent, ethene and oxygen Preferably, for separating the ethene oxide as valuable product from the effluent stream, the ethene and the oxygen preferably comprised in the effluent stream are suitably separated from the effluent stream. It is preferred that the process further comprised (iv) separating ethene and oxygen from the effluent stream, obtaining a stream S1 which, relative to the effluent stream, is enriched in ethene oxide, the solvent, and water.

Generally, the separating according to (iv) will be carried out so that preferably at least 95 weight-%, more preferably at least 98 weight-%, more preferably at least 99 weight-% of S1 consist of ethene oxide, the solvent, and water. While there are no specific restrictions how the separating according to (iv) is carried out, it is preferred that a fractionation unit, more preferably a distillation unit is used wherein S1 is preferably obtained as the bottoms streams.

Preferably, from (iv), a stream is obtained which, relative to the effluent stream, is enriched in ethene and oxygen. More preferably, this stream is obtained as stream from the fractionation unit, more preferably from the distillation unit, preferably as top stream. Regarding this stream, it may be preferred to reduce its oxygen content. No specific restrictions exist how the oxygen content of this stream is reduced. For example, it may be preferred that the stream enriched in ethene and oxygen is reacted with hydrogen. Therefore, the process may further comprise (iv-2) reducing the oxygen content of the stream enriched in ethene and oxygen, preferably comprising reacting the oxygen comprised in the stream with hydrogen, obtaining a stream comprising ethene and depleted in oxygen compared to the stream enriched in ethene and oxygen.

Preferably, the oxygen is reacted with hydrogen in the presence of a catalyst, said catalyst preferably comprising copper in elemental form, oxidic form, or elemental and oxidic form, on a support, wherein copper is present on the support preferably in an amount of 30 to 80 weight-% based on the whole catalyst and calculated as CuO. The thus obtained stream which comprises ethene and which is depleted in oxygen may be preferably recycled, more preferably recycled to (i). Prior to recycling to (i), it is conceivable that the stream which comprises ethene and which is depleted in oxygen is subjected to one or more further steps, such as suitable purification steps.

Preferably, the stream S1 obtained according to (iv) is subjected to further purification relative to the valuable product ethene oxide. More preferably, the process further comprises (v) separating ethene oxide from the stream S1, obtaining a stream S11 comprising ethene oxide and depleted of the solvent and water compared to the stream S1, and obtaining a stream S12 enriched in the solvent and water compared to the stream S1.

While there are no specific restrictions how the separating according to (v) is carried out, it is preferred that a fractionation unit, more preferably a distillation unit is used wherein S1 is preferably obtained as the bottoms streams wherein the stream S11 comprising ethene oxide and depleted of the solvent and water is preferably obtained as top stream and wherein the stream S12 enriched in the solvent and water is preferably obtained as bottoms stream.

From (v), the stream S11 is obtained which, relative to the stream S1, is enriched in ethene oxide. Regarding this stream, it may be preferred to further reduce its oxygen content of, for example, the solvent and water. No specific restrictions exist how this further reducing is carried out. For example, it may be preferred that the stream S11 is reacted to further fractionation. Therefore, the process may further comprise (v-2) subjecting the stream S11 comprising ethene oxide and depleted of the solvent and water to further purification with regard to ethene oxide, preferably in a fractionation unit, more preferably in a distillation unit.

From (v), the stream S12 is obtained which, relative to the stream S1, is enriched in the solvent and water. This stream may be preferably recycled, more preferably recycled to (i). Prior to recycling to (i), it is conceivable that the stream S12 is subjected to one or more further steps, such as one or more work-up stages, for example one or more suitable purification steps.

Use

Further, the present invention also relates to the use of a catalyst comprising a titanium zeolite comprising zinc and having framework type MWW for the epoxidation of ethene, preferably for the liquid-phase epoxidation of ethene. Regarding a preferred use, hydrogen peroxide is employed as epoxidation agent. Regarding a further preferred use, the liquid-phase epoxidation of ethene is carried out in a solvent, preferably comprising, more preferably being, acetonitrile.

Catalytic System

Yet further, the present invention relates to a catalytic system for the epoxidation of ethene, wherein the catalytic system comprises a catalyst comprising a titanium zeolite comprising zinc and having framework type MWW, and further comprises a dissolved potassium salt, and wherein the catalytic system is obtainable or obtained by (i) providing a liquid feed stream comprising ethene, hydrogen peroxide, a solvent and a dissolved potassium salt;

(ii) passing the liquid feed stream provided in (i) into an epoxidation zone comprising a catalyst comprising a titanium zeolite comprising zinc and having framework type MWW, and subjecting the liquid feed stream to epoxidation reaction conditions in the epoxidation zone, obtaining a reaction mixture comprising ethene oxide, water, the solvent and the a dissolved potassium salt.

Regarding preferred solvents and preferred potassium salts, reference is made to the respective disclosure hereinabove.

The present invention is further illustrated by the following set of embodiments and combinations of embodiments resulting from the given dependencies and back-references.

0. A process for preparing ethene oxide, comprising
 (i) providing a liquid feed stream comprising ethene, hydrogen peroxide, and a solvent;
 (ii) passing the liquid feed stream provided in (i) into an epoxidation zone comprising a catalyst comprising a titanium zeolite having framework type MWW and comprising at least one additional heteroatom other than Ti, preferably one or more of Zr, V, Nb, Ta, Cr, Mo, W, Mn, Fe, Co, Ni, Zn, Ga, Ge, In, Sn, Pb, and subjecting the liquid feed stream to epoxidation reaction conditions in the epoxidation zone, obtaining a reaction mixture comprising ethene oxide, water, and the solvent;
 (iii) removing an effluent stream from the epoxidation zone, the effluent stream comprising ethene oxide, water, and the solvent.

1. A process for preparing ethene oxide, preferably the process of embodiment 0, comprising
 (i) providing a liquid feed stream comprising ethene, hydrogen peroxide, and a solvent;
 (ii) passing the liquid feed stream provided in (i) into an epoxidation zone comprising a catalyst comprising a titanium zeolite comprising zinc and having framework type MWW, and subjecting the liquid feed stream to epoxidation reaction conditions in the epoxidation zone, obtaining a reaction mixture comprising ethene oxide, water, and the solvent;
 (iii) removing an effluent stream from the epoxidation zone, the effluent stream comprising ethene oxide, water, and the solvent.

2. The process of embodiment 1, being a process for continuously preparing ethene oxide, comprising
    (i) continuously providing a liquid feed stream comprising ethene, hydrogen peroxide, and a solvent;
    (ii) continuously passing the liquid feed stream provided in (i) into an epoxidation zone comprising a catalyst comprising a titanium zeolite comprising zinc and having framework type MWW, and subjecting the liquid feed stream to epoxidation reaction conditions in the epoxidation zone, obtaining a reaction mixture comprising ethene oxide, water, and the solvent;
    (iii) continuously removing an effluent stream from the epoxidation zone, the effluent stream comprising ethene oxide, water, and the solvent.

3. The process of embodiment 1 or 2, wherein in the liquid feed stream provided in (i), the molar ratio of ethene relative to hydrogen peroxide is in the range of from 1:1 to 5:1, preferably in the range of from 1:1 to 3:1, more preferably in the range of from 1:1 to 2:1, more preferably in the range of from 1:1 to 1.5:1.

4. The process of any one of embodiments 1 to 3, wherein the liquid feed stream provided in (i) comprises the ethene in an amount in the range of from 5 to 30 weight-%, preferably in the range of from 6 to 20 weight-%, more preferably in the range of from 7 to 15 weight-%, based on the total weight of the liquid feed stream.

5. The process of any one of embodiments 1 to 4, wherein the solvent comprises one or more organic solvents, preferably one or more of tert-butanol, propylene carbonate, methylacetate, and acetonitrile, more preferably acetonitrile, wherein more preferably, the solvent is acetonitrile.

6. The process of any one of embodiments 1 to 5, wherein the liquid feed stream provided in (i) comprises the solvent in an amount in the range of from 60 to 85 weight-%, preferably in the range of from 62 to 83 weight-%, more preferably in the range of from 65 to 80 weight-%, based on the total weight of the liquid feed stream.

7. The process of any one of embodiments 1 to 6, wherein the liquid feed stream provided in (i) further comprises water.

8. The process of any one of embodiments 1 to 7, wherein the liquid feed stream provided in (i) further comprises one or more alkenes in addition to ethene.

9. The process of embodiment 8, wherein the one or more alkenes comprised in the liquid feed stream in addition to ethene comprise propene.

10. The process of embodiment 8 or 9, wherein in the liquid feed stream provided in (i), the molar ratio of ethene relative to the sum of the one or more further alkenes is in the range of from 100:1.0 to 100:0.1.

11. The process of any one of embodiments 1 to 10, wherein the liquid feed stream provided in (i) further comprises one or more alkanes.

12. The process of embodiment 11, wherein the one or more alkanes comprise one or more of methane and ethane.

13. The process of embodiment 11 or 12, wherein in the liquid feed stream provided in (i), the molar ratio of ethene relative to the sum of the one or more alkanes is in the range of from 100:2.0 to 100:0.1.

14. The process of any one of embodiments 1 to 13, wherein at least 95 weight-%, preferably at least 98 weight-%, more preferably at least 99 weight-% of the liquid feed stream provided in (i) consist of ethene, hydrogen peroxide, the solvent, and water.

15. The process of any one of embodiments 1 to 14, wherein the liquid feed stream provided in (i) further comprises a dissolved salt, preferably a dissolved potassium salt.

16. The process of embodiment 15, wherein the potassium salt is one or more of an inorganic potassium salt and an organic potassium salt.

17. The process of embodiment 15 or 16, wherein the inorganic potassium salt is one or more of potassium hydroxide, a potassium halide, potassium nitrate, potassium sulfate, potassium hydrogen sulfate, potassium perchlorate, and a potassium salt of a phosphorus oxyacid.

18. The process of embodiment 17, wherein the potassium salt of a phosphorus oxyacid has the formula $K_{nx}H_{2+n(1-x)}P_nO_{3n+1}$, wherein n is an integer in the range of from 1 to 10, preferably in the range of from 1 to 5, more preferably in the range of from 1 to 3, and wherein x is in the range of from 0.6 to 1.4, preferably in the range of from 0.7 to 1.3, more preferably in the range of from 0.8 to 1.2, wherein more preferably, n is 1 and x is in the range of from 0.95 to 1.05.

19. The process of any one of embodiments 16 to 18, wherein the organic potassium salt is one or more of aliphatic saturated monocarboxylic acids preferably having 1, 2, 3, 4, 5 or 6 carbon atoms, potassium carbonate, and potassium hydrogen carbonate, preferably one or more of potassium formate and potassium acetate.

20. The process of any one of embodiments 16 to 19, wherein the organic potassium salt comprises, preferably is, potassium formate.

21. The process of any one of embodiments 15 to 20, wherein in the liquid feed stream provided in (i), the molar ratio of the dissolved salt relative to the hydrogen peroxide is in the range of from $25 \times 10^{-6}:1$ to $500 \times 10^{-6}:1$, preferably in the range of from $50 \times 10^{-6}:1$ to $250 \times 10^{-6}:1$, more preferably in the range of from $100 \times 10^{-6}:1$ to $150 \times 10^{-6}:1$.

22. The process of any one of embodiments 15 to 21, wherein at least 95 weight-%, preferably at least 98 weight-%, more preferably at least 99 weight-% of the liquid feed stream provided in (i) consist of ethene, hydrogen peroxide, the solvent, water, and the dissolved salt.

23. The process of any one of embodiments 1 to 22, wherein the liquid feed stream provided in (i) is under a pressure in the range of from 18 to 60 bar(abs), preferably in the range of from 30 to 60 bar(abs), more preferably in the range of from 35 to 55 bar(abs), more preferably in the range of from 40 to 50 bar(abs).

24. The process of any one of embodiments 1 to 23, wherein the liquid feed stream provided in (i) has a temperature in the range of from 20 to 60° C., preferably in the range of from 25 to 50° C., more preferably in the range of from 30 to 45° C.

25. The process of any one of embodiments 1 to 24, wherein in the epoxidation zone according to (ii), the reaction mixture is liquid under the epoxidation conditions.

26. The process of any one of embodiment 1 to 25, wherein in the epoxidation zone according to (ii), the reaction mixture consists of one single liquid phase under the epoxidation conditions.

27. The process of any one of embodiments 1 to 26, wherein the epoxidation zone according to (ii) comprises a first epoxidation subzone consisting of one or more epoxidation reactors A, wherein, if the first epoxidation subzone comprises two or more epoxidation reactors A, the two or more epoxidation reactors A are arranged in parallel, and wherein in (ii), the liquid feed stream provided in (i) is passed into at least one of the epoxidation reactors A.

28. The process of embodiment 27, wherein the epoxidation zone according to (ii) consists of the first epoxidation subzone.

29. The process of 27 or 28, wherein the epoxidation conditions according to (ii) comprise an epoxidation temperature in the first epoxidation subzone in the range of from 20 to 60° C., preferably in the range of from 25 to 50° C., more preferably in the range of from 30 to 45° C., wherein said epoxidation temperature is defined as the temperature of a heat transfer medium used for adjusting the temperature of the reaction mixture in the first epoxidation reaction subzone, preferably by passing the heat transfer medium through a jacket of the one or more epoxidation reactors A, wherein said epoxidation temperature is preferably the temperature of the heat transfer medium prior to adjusting the temperature of the reaction mixture, more preferably the temperature of the heat transfer medium at the entrance of the jacket of the one or more epoxidation reactors A.

30. The process of any one of embodiments 27 to 29, wherein the epoxidation conditions according to (ii) comprise a first epoxidation reaction pressure in the range of from 18 to 60 bar(abs), preferably in the range of from 30 to 60 bar(abs), preferably in the range of from 35 to 55 bar(abs), more preferably in the range of from 40 to 50 bar(abs), wherein the first epoxidation reaction pressure is defined as the absolute pressure at the exit of the first epoxidation subzone.

31. The process of any one of embodiments 27 to 30, wherein the epoxidation conditions according to (ii) comprise a catalyst loading in the first epoxidation subzone in the range of from 0.05 to 1.25 $h^{-1}$, preferably in the range of from 0.1 to 1 $h^{-1}$, more preferably in the range of from 0.2 to 0.7 $h^{-1}$, wherein the catalyst loading is defined as the ratio of the mass flow rate in kg/h of hydrogen peroxide contained in liquid feed stream provided in (i) relative to the amount in kg of catalyst comprising a titanium zeolite comprising zinc and having framework type MWW comprised in the first epoxidation subzone according to (ii).

32. The process of any one of embodiments 27 to 31, wherein the epoxidation zone according to (ii) additionally comprises a second epoxidation subzone consisting of one or more epoxidation reactors B wherein, if the second epoxidation subzone comprises two or more epoxidation reactors B, the two or more epoxidation reactors B are arranged in parallel, wherein the second epoxidation subzone is arranged downstream of the first epoxidation subzone.

33. The process of embodiment 32, wherein the epoxidation zone according to (ii) consists of the first epoxidation subzone and the second epoxidation subzone.

34. The process of embodiment 32 or 33, wherein the epoxidation conditions according to (ii) comprise a second epoxidation reaction pressure in the range of from 18 to 60 bar(abs), preferably in the range of from 30 to 60 bar (abs), preferably in the range of from 35 to 55 bar(abs), more preferably in the range of from 40 to 50 bar(abs), wherein the first epoxidation reaction pressure is defined as the absolute pressure at the exit of the second epoxidation subzone.

35. The process of any one of embodiments 32 to 34, wherein the epoxidation conditions according to (ii) comprise a catalyst loading in the second epoxidation subzone in the range of from 0.001 to 0.5 $h^{-1}$, preferably in the range of from 0.005 to 0.3 $h^{-1}$, more preferably in the range of from 0.01 to 0.2 $h^{-1}$, wherein the catalyst loading is defined as the ratio of the mass flow rate in kg/h of hydrogen peroxide contained in the feed stream passed into the second epoxidation subzone relative to the amount in kg of catalyst comprising a titanium zeolite comprising zinc and having framework type MWW comprised in the second epoxidation subzone according to (ii).

36. The process of any one of embodiments 32 to 35, wherein the temperature of the reaction mixture in the second epoxidation reaction subzone is not adjusted by passing a heat transfer medium through a jacket of the one or more epoxidation reactors B, wherein preferably, the second epoxidation subzone is an essentially adiabatic epoxidation subzone, more preferably an adiabatic epoxidation subzone.

37. The process of any one of embodiments 1 to 36, wherein according to (ii), the catalyst comprising a titanium zeolite comprising zinc and having framework type MWW is present in the epoxidation zone as a fixed-bed catalyst, preferably having a tortuosity parameter relative to water of at most 4 determined as described in Reference Example 1.1.

38. The process of any one of embodiments 1 to 37, wherein the titanium zeolite comprising zinc and having framework type MWW comprised in the catalyst according to (ii) comprises titanium, calculated as elemental titanium, in an amount in the range of from 0.1 to 5 weight-%, preferably in the range of from 1 to 3 weight-%, based on the total weight of the titanium zeolite comprising zinc and having framework type MWW.

39. The process of any one of embodiments 1 to 38, wherein the titanium zeolite having framework type MWW comprised in the catalyst according to (ii) comprises zinc, calculated as elemental zinc, in an amount in the range of from 0.1 to 5 weight-%, preferably in the range of from 1 to 3 weight-%, based on the total weight of the titanium zeolite comprising zinc and having framework type MWW.

40. The process of any one of embodiments 1 to 39, wherein at least 98 weight-%, preferably at least 99 weight-%, more preferably at least 99.9 weight-% of the titanium zeolite comprising zinc and having framework type MWW consist of Zn, Ti, Si, O, and H.

41. The process of any one of embodiments 1 to 40, wherein the catalyst comprising the titanium zeolite comprising zinc and having framework type MWW is in the form of a molding, comprising the titanium zeolite having framework type MWW and a binder, preferably a silica binder.

42. The process of embodiment 41, wherein the catalyst comprising the titanium zeolite comprising zinc and having framework type MWW comprises the titanium zeolite comprising zinc and having framework type MWW preferably in an amount in the range of from 70 to 80 weight-%, based on the total weight of the catalyst, and the silica binder preferably in an amount of from 30 to 20 weight-%, based on the total weight of the catalyst, wherein preferably at least 99 weight-% of the catalyst consist of the titanium zeolite comprising zinc and having framework type MWW and the binder.

43. The process of any one of embodiments 1 to 42, wherein the epoxidation conditions according to (ii) comprise a hydrogen peroxide conversion in the range of from 85 to 100%, preferably in the range of from 90 to 100%, more preferably in the range of from 95 to 100%, wherein the hydrogen peroxide conversion is defined as 100×(1−y) %, wherein y is the molar amount of hydrogen peroxide comprised in the effluent stream removed in (iii) relative to the molar amount of hydrogen peroxide comprised in the liquid feed stream provided in (i).

44. The process of any one of embodiments 1 to 43, wherein the ethene oxide selectivity S(HP) of the epoxidation reaction in the epoxidation reaction zone according to (ii) is in the range of from 80 to 100%, preferably in the range of from 85 to 100%, more preferably in the range of from 90 to 100%, wherein the ethene oxide selectivity S(HP) is defined as the molar amount of ethene oxide comprised in the effluent stream removed in (iii) relative to the molar amount of hydrogen peroxide comprised in the liquid feed stream provided in (i).

45. The process of any one of embodiments 1 to 44, wherein the ethene oxide selectivity S(ET) of the epoxidation reaction in the epoxidation reaction zone according to (ii) is in the range of from 85 to 100%, preferably in the range of from 90 to 100%, more preferably in the range of from 95 to 100%, wherein the ethene oxide selectivity S(ET) is defined as the molar amount of ethene oxide comprised in the effluent stream removed in (iii) relative to the molar amount of hydrogen peroxide comprised in the liquid feed stream provided in (i).

46. The process of any one of embodiments 1 to 45, wherein the effluent stream removed in (iii) comprises carbon dioxide in an amount in the range of from 100 to 1500 weight-ppm, preferably in the range of from 150 to 1200 weight-ppm, more preferably in the range of from 200 to 1000 weight-ppm, based on the total weight of the effluent stream.

47. The process of any one of embodiments 1 to 46, wherein the effluent stream removed in (iii) comprises ethene oxide, water, the solvent, ethene, and oxygen.

48. The process of embodiment 47, further comprising (iv) separating ethene and oxygen from the effluent stream, obtaining a stream S1 which, relative to the effluent stream, is enriched in ethene oxide, the solvent, and water.

49. The process of embodiment 48, wherein at least 95 weight-%, preferably at least 98 weight-%, more preferably at least 99 weight-% of S1 consist of ethene oxide, the solvent, and water, wherein for the separating in (iv), preferably a fractionation unit, more preferably a distillation unit is used and wherein S1 is preferably obtained as bottoms streams.

50. The process of embodiment 48 or 49, wherein in (iv), a stream is obtained, preferably as top stream in the fractionation unit according to embodiment 49, which, relative to the effluent stream, is enriched in ethene and oxygen.

51. The process of embodiment 50, further comprising (iv-2) reducing the oxygen content of the stream enriched in ethene and oxygen, preferably comprising reacting the oxygen comprised in the stream with hydrogen, obtaining a stream comprising ethene and depleted in oxygen compared to the stream enriched in ethene and oxygen.

52. The process of embodiment 51, wherein the oxygen is reacted with hydrogen in the presence of a catalyst, said catalyst preferably comprising copper in elemental form, oxidic form, or elemental and oxidic form, on a support, wherein copper is present on the support preferably in an amount of 30 to 80 weight-% based on the whole catalyst and calculated as CuO.

53. The process of embodiment 51 or 52, wherein the stream comprising ethene and depleted in oxygen is recycled, optionally after one or more work-up stages, to (i).

54. The process of any one of embodiments 48 to 53, further comprising (v) separating ethene oxide from the stream S1, obtaining a stream S11 comprising ethene oxide and depleted of the solvent and water compared to the stream S1, and obtaining a stream S12 enriched in the solvent and water compared to the stream S1.

55. The process of embodiment 54, wherein for the separating in (v), a fractionation unit, preferably a distillation unit is used, wherein the stream S11 comprising ethene oxide and depleted of the solvent and water is preferably obtained as top stream and wherein the stream S12 enriched in the solvent and water is preferably obtained as bottoms stream.

56. The process of embodiment 54 or 55, further comprising (v-2) subjecting the stream S11 comprising ethene oxide and depleted of the solvent and water to further purification with regard to ethene oxide, preferably in a fractionation unit, more preferably in a distillation unit.

57. The process of any one of embodiments 54 to 56, wherein the stream S12 enriched in the solvent and water is recycled, optionally after one or more work-up stages, to (i).

58. Use of a catalyst comprising a titanium zeolite comprising zinc and having framework type MWW for the epoxidation of ethene, preferably for the liquid-phase epoxidation of ethene.

59. The use of embodiment 58, wherein the liquid-phase epoxidation of ethene is carried out in a solvent, preferably in acetonitrile as the solvent.

60. The use of embodiment 58 or 59, wherein hydrogen peroxide is employed as epoxidation agent.

61. A method for epoxidizing ethene, preferably in the liquid phase, wherein ethene is epoxidized in the presence of a catalyst comprising a titanium zeolite comprising zinc and having framework type MWW.

62. The method of embodiment 61, wherein the liquid-phase epoxidation of ethene is carried out in a solvent, preferably in acetonitrile as the solvent.

63. The method of embodiment 61 or 62, wherein hydrogen peroxide is employed as epoxidation agent.

64. A catalytic system for the epoxidation of ethene, comprising a catalyst comprising a titanium zeolite comprising zinc and having framework type MWW, said catalytic system further comprising a dissolved potassium salt and being obtainable or obtained by (i) providing a liquid feed stream comprising ethene, hydrogen peroxide, a solvent and a a dissolved potassium salt and;

(ii) passing the liquid feed stream provided in (i) into an epoxidation zone comprising a catalyst comprising a titanium zeolite comprising zinc and having framework type MWW, and subjecting the liquid feed stream to epoxidation reaction conditions in the epoxidation zone, obtaining a reaction mixture comprising ethene oxide, water, the solvent and the a dissolved potassium salt and.

65. The catalytic system of embodiment 64, wherein the titanium zeolite comprising zinc and having framework type MWW comprised in the catalyst in (ii) contains titanium, calculated as elemental titanium, in an amount in the range of from 0.1 to 5 weight-%, preferably in the range of from 1 to 3 weight-%, based on the total weight of the titanium zeolite comprising zinc and having framework type MWW, and contains zinc, calculated as elemental zinc, in an amount in the range of from 0.1 to 5 weight-%, preferably from 1 to 3 weight-%, based on the total weight of the titanium zeolite comprising zinc and having framework type MWW.

66. The catalytic system of embodiment 64 or 65, wherein the dissolved potassium salt is one or more of potassium hydroxide, a potassium halide, potassium nitrate, potassium sulfate, potassium hydrogen sulfate, potassium perchlorate, a potassium salt of a phosphorus oxyacid, potassium formate, and potassium acetate The present invention is further illustrated by the following reference examples and examples.

EXAMPLES

Reference Example 1: Determination of Catalyst Characteristics

Reference Example 1.1: Determination of the Tortuosity Parameter

The tortuosity parameter was determined as described in the experimental section of US 20070099299 A1. In particular, the NMR analyses to this effect were conducted at 25° C. and 1 bar at 125 MHz $^1$H resonance frequency with the FEGRIS NT NMR spectrometer (cf. Stallmach et al. in Annual Reports on NMR Spectroscopy 2007, Vol. 61, pp. 51-131) at the Faculty for Physics and Geological Sciences of the University of Leipzig. The pulse program used for the PFG NMR self-diffusion analyses was the stimulated spin echo with pulsed field gradients according to FIG. 1b of US 20070099299 A1. For each sample, the spin echo attenuation curves were measured at up to seven different diffusion times ($\Delta$/ms=7, 10, 12, 25, 50, 75, 100) by stepwise increase in the intensity of the field gradients ($g_{max}$=10 T/m). From the spin echo attenuation curves, the time dependence of the self-diffusion coefficient of the pore water was determined by means of equations (5) and (6) of US 20070099299 A1. Calculation of the Tortuosity Equation (7) of US 20070099299 A1 was used to calculate the time dependency of the mean quadratic shift $$\langle z^2(\Delta) \rangle = \tfrac{1}{3} \langle r^2(\Delta) \rangle$$

from the self-diffusion coefficients D($\Delta$) thus determined. By way of example, in FIG. 2 of US 20070099299 A1, the data is plotted for exemplary catalyst supports of said document in double logarithmic form together with the corresponding results for free water. FIG. 2 of US 20070099299 A1 also shows in each case the best fit straight line from the linear fitting of $$\langle r^2(\Delta) \rangle$$

as a function of the diffusion time $\Delta$. According to equation (7) of US 2007/0099299 A1, its slope corresponds precisely to the value 6 $\overline{D}$ where $\overline{D}$ corresponds to the self-diffusion coefficient averaged over the diffusion time interval. According to equation (3) of US 20070099299 A1, the tortuosity is then obtained from the ratio of the mean self-diffusion coefficient of the free solvent ($D_0$) thus determined to the corresponding value of the mean self-diffusion coefficient in the molding.

Reference Example 1.2: Determination of Dv10, Dv50, and Dv90 Values 1.0 g of the micropowder is suspended in 100 g deionized water and stirred for 1 min. The sample was subjected to the measurement in an apparatus using the following parameters: Mastersizer S long bed version 2.15, ser. No. 33544-325; supplier: Malvern Instruments GmbH, Herrenberg, Germany: focal width 300 RF mm; beam length 10.00 mm; module MS17; shadowing 16.9%; dispersion model 3$$D; analysis model polydisperse correction none.

Reference Example 1.3: Determination of the Silanol Concentration of the Moldings of the Present Invention For the determination of the silanol concentration, the $^{29}$Si MAS NMR experiments were carried out at room temperature on a VARIAN Infinityplus-400 spectrometer using 5.0 mm ZrO$_2$ rotors. The $^{29}$Si MAS NMR spectra were collected at 79.5 MHz using a 1.9 µs π/4 (microsecond pi/4) pulse with 10 s recycle delay and 4000 scans. All $^{29}$Si spectra were recorded on samples spun at 6 kHz, and chemical shifts were referenced to 4,4-dimethyl-4-silapentane sulfonate sodium (DSS). For the determination of the silanol group concentration, a given $^{29}$Si MAS NMR spectrum is deconvolved by the proper Gaussian-Lorentzian line shapes. The concentration of the silanol groups with respect to the total number of Si atoms is obtained by integrating the deconvolved $^{29}$Si MAS NMR spectra.

Reference Example 1.4: Determination of the Crush Strength of the Moldings

The crush strength as referred to in the context of the present invention is to be understood as determined via a crush strength test machine Z2.5/TS1S, supplier Zwick GmbH & Co., D-89079 Ulm, Germany. As to fundamentals of this machine and its operation, reference is made to the respective instructions handbook "Register 1: Betriebsanleitung/Sicherheitshandbuch für die Material-Prüfmaschine Z2.5/TS1S", version 1.5, December 2001 by Zwick GmbH & Co. Technische Dokumentation, August-Nagel-Strasse 11, D-89079 Ulm, Germany. With said machine, a given strand is subjected to an increasing force via a plunger having a diameter of 3 mm until the strand is crushed. The force at which the strand crushes is referred to as the crushing strength of the strand. The machine is equipped with a fixed horizontal table on which the strand is positioned. A plunger which is freely movable in vertical direction actuates the strand against the fixed table. The apparatus was operated with a preliminary force of 0.5 N, a shear rate under preliminary force of 10 mm/min and a subsequent testing rate of 1.6 mm/min. The vertically movable plunger was connected to a load cell for force pick-up and, during the measurement, moved toward the fixed turntable on which the molding (strand) to be investigated is positioned, thus actuating the strand against the table. The plunger was applied to the stands perpendicularly to their longitudinal axis. Controlling the experiment was carried out by means of a computer which registered and evaluated the results of the measurements. The values obtained are the mean value of the measurements for 10 strands in each case.

Reference Example 1.5: $^{29}$Si Solid-State NMR Spectra Regarding Q$^3$ and Q$^4$ Structures The effect of the inventive water treatment on the molding related to Q$^3$ and Q$^4$ structures in the material was characterized by comparing the changes in $^{29}$Si solid-state NMR spectra under comparable conditions. All $^{29}$Si solid-state NMR experiments were performed using a Bruker Advance spectrometer with 300 MHz $^1$H Larmor frequency (Bruker Biospin, Germany). Samples were packed in 7 mm ZrO$_2$ rotors, and measured under 5 kHz Magic Angle Spinning at room temperature. $^{29}$Si direct polarization spectra were obtained using (pi/2)-pulse excitation with 5 microsecond pulse width, a $^{29}$Si carrier frequency corresponding to −65 ppm in the spectrum, and a scan recycle delay of 120 s. Signal was acquired for 25 ms under 45 kHz high-power proton decoupling, and accumulated over 10 to 17 hours. Spectra were processed using Bruker Topspin with 30 Hz exponential line broadening, manual phasing, and manual baseline correction over the full spectrum width. Spectra were referenced with the polymer Q8M8 as an external secondary standard, setting the resonance of the trimethylsilyl M group to 12.5 ppm. The spectra were then fitted with a set of Gaussian line shapes, according to the number of discernable resonances. Relating to the presently assessed spectra, 6 lines in total were used, accounting for the five distinct peak maxima (at approximately −118, −115, −113, −110 and −104 ppm) plus the clearly visible shoulder at −98 ppm. Fitting was performed using DMFit (Massiot et al., Magnetic Resonance in Chemistry, 40 (2002) pp 70-76). Peaks were manually set at the visible peak maxima or shoulder. Both peak position and line width were then left unrestrained, i.e., fit peaks were not fixed at a certain position. The fitting outcome was numerically stable, i.e., distortions in the initial fit setup as described above did lead to similar results. The fitted peak areas were further used normalized as done by DMFit. After the water treatment of the invention, a decrease of signal intensity at the left hand side of the spectrum was observed, a region that includes $Q^3$ silanol structures (here especially: around and above −104 ppm, i.e. "left" of −104 ppm). Further, an increase of signal at the right hand side of the spectrum (here: below −110 ppm, i.e. "right" of −110 ppm) was observed, which region comprises $Q^4$ structures exclusively. For the quantification of spectrum changes, a ratio was calculated that reflects changes in the peak areas "left hand" and "right hand", as follows. The six peaks were labeled with 1, 2, 3, 4, 5, and 6, and the ratio Q was calculated with the formula $100*\{[a_1+a_2]/[a_4+a_5+a_6]\}/a_3$. In this formula, $a_{i,\ i=1\ldots 6}$ represents the area of the fitted peak to which this number was attributed.

Reference Example 1.6: Water Adsorption/Desorption—Water Uptake

The water adsorption/desorption isotherms measurements were performed on a VTI SA instrument from TA Instruments following a step-isotherm program. The experiment consisted of a run or a series of runs performed on a sample material that has been placed on the microbalance pan inside of the instrument. Before the measurement were started, the residual moisture of the sample was removed by heating the sample to 100° C. (heating ramp of 5° C./min) and holding it for 6 h under a $N_2$ flow. After the drying program, the temperature in the cell was decreased to 25° C. and kept isothermal during the measurements. The microbalance was calibrated, and the weight of the dried sample was balanced (maximum mass deviation 0.01 weight-%). Water uptake by the sample was measured as the increase in weight over that of the dry sample. First, an adsorption curve was measured by increasing the relative humidity (RH) (expressed as weight-% water in the atmosphere inside of the cell) to which the samples was exposed and measuring the water uptake by the sample at equilibrium. The RH was increased with a step of 10 weight-% from 5 to 85% and at each step the system controlled the RH and monitored the sample weight until reaching the equilibrium conditions and recording the weight uptake. The total adsorbed water amount by the sample was taken after the sample was exposed to the 85 weight-% RH. During the desorption measurement the RH was decreased from 85 weight-% to 5 weight-% with a step of 10% and the change in the weight of the sample (water uptake) was monitored and recorded.

Reference Example 1.7: FT-IR Measurements

The FT-IR (Fourier-Transformed-Infrared) measurements were performed on a Nicolet 6700 spectrometer. The molding was powdered and then pressed into a self-supporting pellet without the use of any additives. The pellet was introduced into a high vacuum (HV) cell placed into the FT-IR instrument. Prior to the measurement the sample was pretreated in high vacuum ($10^{-5}$ mbar) for 3 h at 300° C. The spectra were collected after cooling the cell to 50° C. The spectra were recorded in the range of 4000 to 800 $cm^{-1}$ at a resolution of 2 $cm^{-1}$. The obtained spectra are represented in a plot having on the x axis the wavenumber ($cm^{-1}$) and on the y axis the absorbance (arbitrary units, a.u.). For the quantitative determination of the peak heights and the ratio between these peaks a baseline correction was carried out. Changes in the 3000-3900 $cm^{-1}$ region were analyzed and for comparing multiple samples, as reference the band at 1880±5 $cm^{-1}$ was taken.

Reference Example 1.8: Determination of Crystallinity Via XRD

The crystallinity of the zeolitic materials according to the present invention were determined by XRD analysis. The data were collected using a standard Bragg-Brentano diffractometer with a Cu-X-ray source and an energy dispersive point detector. The angular range of 2° to 70° (2 theta) was scanned with a step size of 0.02°, while the variable divergence slit was set to a constant illuminated sample length of 20 mm. The data were then analyzed using TOPAS V4 software, wherein the sharp diffraction peaks were modeled using a Pawley fit containing a unit cell with the following starting parameters: a=14.4 Angstrom (1 Angstrom=$10^{-10}$ m) and c=25.2 Angstrom in the space group P6/mmm. These were refined to fit the data. Independent peaks were inserted at the following positions. 8.4°, 22.4°, 28.2° and 43°. These were used to describe the amorphous content. The crystalline content describes the intensity of the crystalline signal to the total scattered intensity. Included in the model were also a linear background, Lorentz and polarization corrections, lattice parameters, space group and crystallite size.

Reference Example 2: Preparation of an Ethene Epoxidation Catalyst

A catalyst comprising a titanium zeolite comprising zinc and having framework type MWW, was prepared according to example 3 of WO 2013/117536 A, page 76, line 1 to page 78, line 11. The tortuosity parameter of this catalyst relative to water, determined as described in Reference Example 1.1 above, was 2.2+/−0.1.

Reference Example 3: Epoxidation Setup, and Analytics

Epoxidation Setup

The experimental setup consisted of continuous plant with a fixed bed reactor. Feeds and products were weighed and analyzed by gas-chromatography (GC). The microplant was installed in two steel-chambers. All feeds were kept constant and the hydrogen peroxide conversion was maintained at 90±5% by adjusting the temperature and/or the dosage of the potassium salt.

Conversion and temperature were checked and corrected once a day. The experiments were run with excess ethene (1.3 mol/mol $H_2O_2$). Ethylene (technical grade, >99 weight-% of ethylene was supplied in a 400 L pressure vessel. It was fed via pipeline to 2 L buffer vessels. A constant pressure of about 30 bar(abs) in the lecture bottles was maintained by pressing $N_2$ to ensure a steady operation of the feeding pumps and a steady supply of the plant. Solvent (acetonitrile) was supplied in a 200 L drum. Hydrogen peroxide (40 weight-% in water) was stored in pressure vessels (5 L, 5 bar(abs) $N_2$ pressure) with temperature control. Additives such as potassium salt(s) could be added either to the acetonitrile or to the hydrogen peroxide in the buffer vessels. All feed streams were mixed and fed to the epoxidation reactor in an up-flow mode (pressure: 20 bar (abs), temperature: 30 to 80° C.).

The reactor (material: stainless steel 1.4571) was a 1400 mm×10 mm tube with an internal diameter of 7 mm, and a double-jacket for cooling or heating with water. The cooling medium (ethylene glycol/water mixture) was fed in cocurrent and the temperature difference between input and output was less than 1° C. 15 g of the catalyst according to Reference Example 2 above were freshly loaded to the epoxidation reactor (fixed-bed) before starting an experiment. Remaining space in the reactor was filled with inert material.

After release of pressure the reactor effluent stream was fed to a gas-liquid separator from which the liquid phase was pumped into the sewer pipeline. The reactor effluent stream was split into a liquid phase and a gas phase at 15° C./1013 mbar.

Sampling and Analytics

The gas phase was fed to the flare or to an online-GC via a three-way valve. A gas meter and a gas chromatograph for the analysis of the gas phase was allocated to the unit. The composition of the gas phase was double-checked by offline measurements at GMA/C on a regular basis. The liquid phase was collected for mass balancing and further analytics. H2O2 conversion was determined by photometric measurements (titanyl sulfate method) of the H2O2 concentration in the feed stream and the reactor effluent stream. All other components were quantified by gas chromatography. The general accuracy of the selectivity measurement in the described setup was estimated to be around ±2%.

Example 1

The liquid feed stream fed to the epoxidation reactor had the following composition:
ethene: 9.1 weight-% (11.1 g/h)
hydrogen peroxide: 13.8 weight-% (16.7 g/h; 40 weight-% aq.)
water: 20.8 weight-% (25.2 g/h)
potassium salt (potassium formate): 130 micromol/mol hydrogen peroxide
solvent (acetonitrile): 56.2 weight-% (68.0 g/h)

The experiment according to Example 1 was carried out at a mean hydrogen peroxide conversion of 90%. The results are shown in FIG. 2. As can be seen in FIG. 2, the selectivities of ethene oxide remained constantly at around 94% (based on hydrogen peroxide) and 98% (based on ethene), even at temperatures of around 40° C. The main by-products were ethylene glycol (selectivity of around 1%), peroxyethanol (selectivity of around 1.5%) and oxygen (selectivity of around 2%). An offgas analysis showed that no CO2 was formed during the first 1100 hours time on stream.

Example 2

The experiment according to Example 2 was carried out based on the same liquid feed stream as Example 1 (see above) and at a mean hydrogen peroxide conversion of at least 98%. In order to achieve the hydrogen peroxide conversion, the cooling water temperature was increased by around 4° C. in comparison with the experiment in Example 1. The results are shown in FIG. 3. As can be seen in FIG. 3, the selectivities of ethene oxide thereby remained at the constant high level as already observed in Example 1.

CITED LITERATURE

Figure 1:
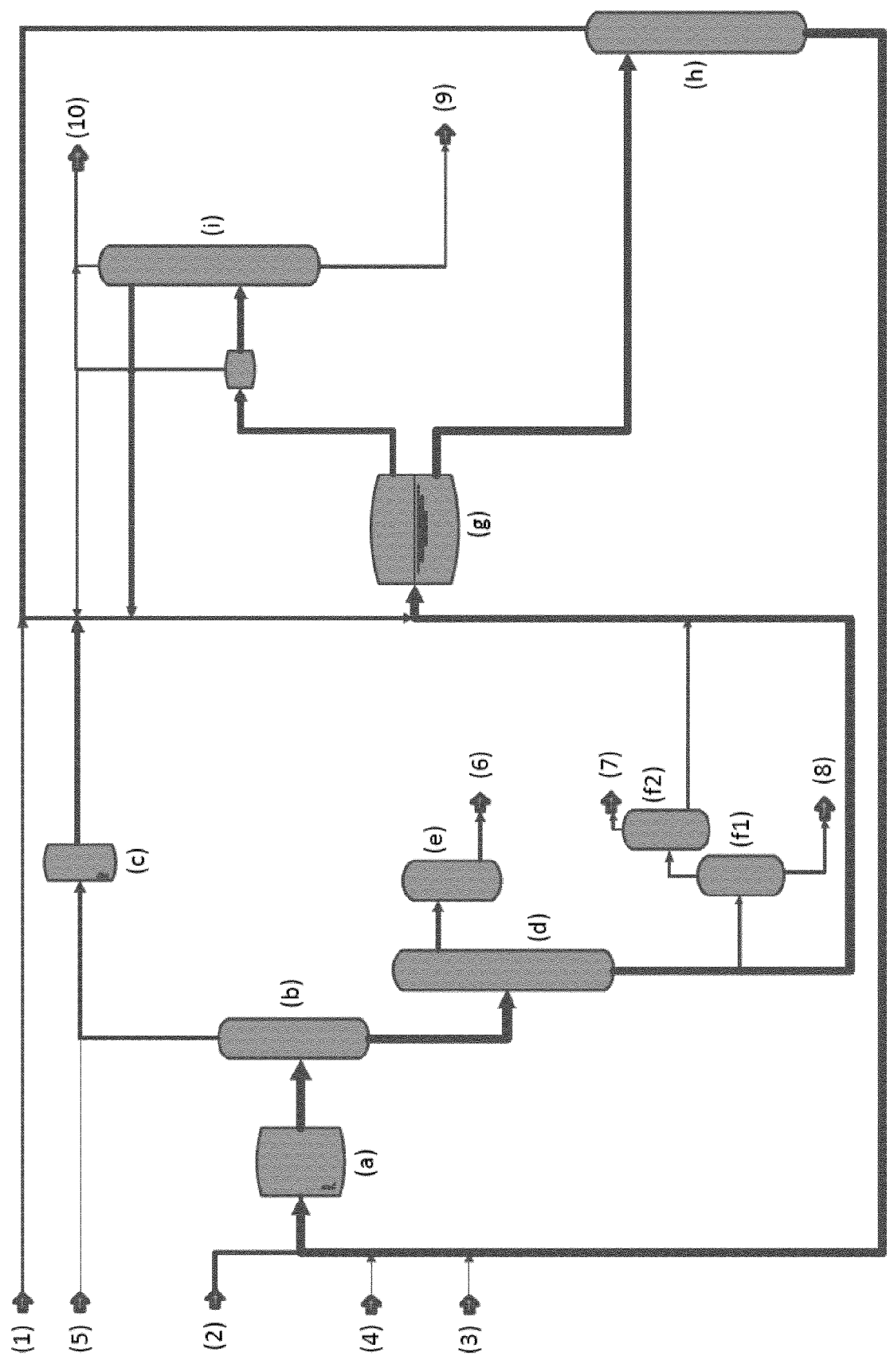
FIG. 1 shows a process flow sheet of the inventive process including a conceivable solvent work-up sequence wherein the abbreviations have the following meanings:
(1) ethene stream
(2) hydrogen peroxide stream
(3) (make-up) solvent stream
(4) stream comprising potassium salt
(5) hydrogen ($H_2$) stream
(6) ethene oxide (product) stream
(7) light boilers stream
(8) heavy boilers stream
(9) waste water stream
(10) offgas stream
(a) epoxidation unit (first epoxidation subzone)
(b) oxygen ($O_2$) and ethene separation unit
(c) hydrogenation unit (ethene recycling)
(d) solvent separation unit
(e) ethene oxide purification unit
(f1)(f2) first solvent work-up unit (part-stream distillation unit)
(g) second solvent work-up unit (phase separation water/solvent)
(h) third solvent work-up unit (solvent distillation)
(i) fourth solvent work-up unit (water separation)
Figure 2:
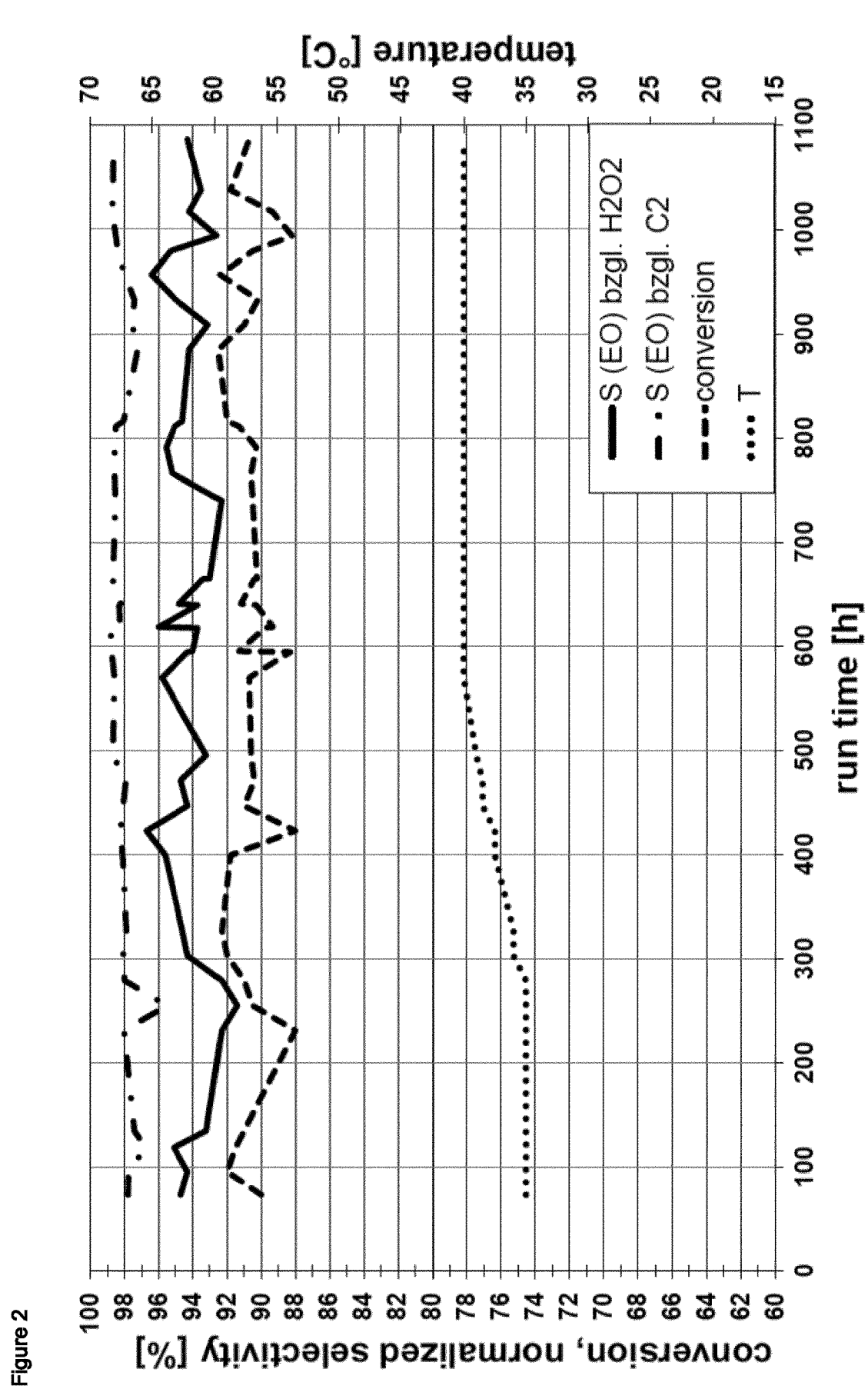
FIG. 2 shows the selectivities of ethene oxide during the first 1100 hours time on stream of the epoxidation reaction as described in Example 1. The left hand Y axis shows the conversion of hydrogen peroxide in % and the normalized selectivities of ethene oxide based on hydrogen peroxide and based on ethene, respectively, both in %. The right hand Y axis shows the temperature in ° C. Further reference is made to the legend in FIG. 2.
Figure 3:
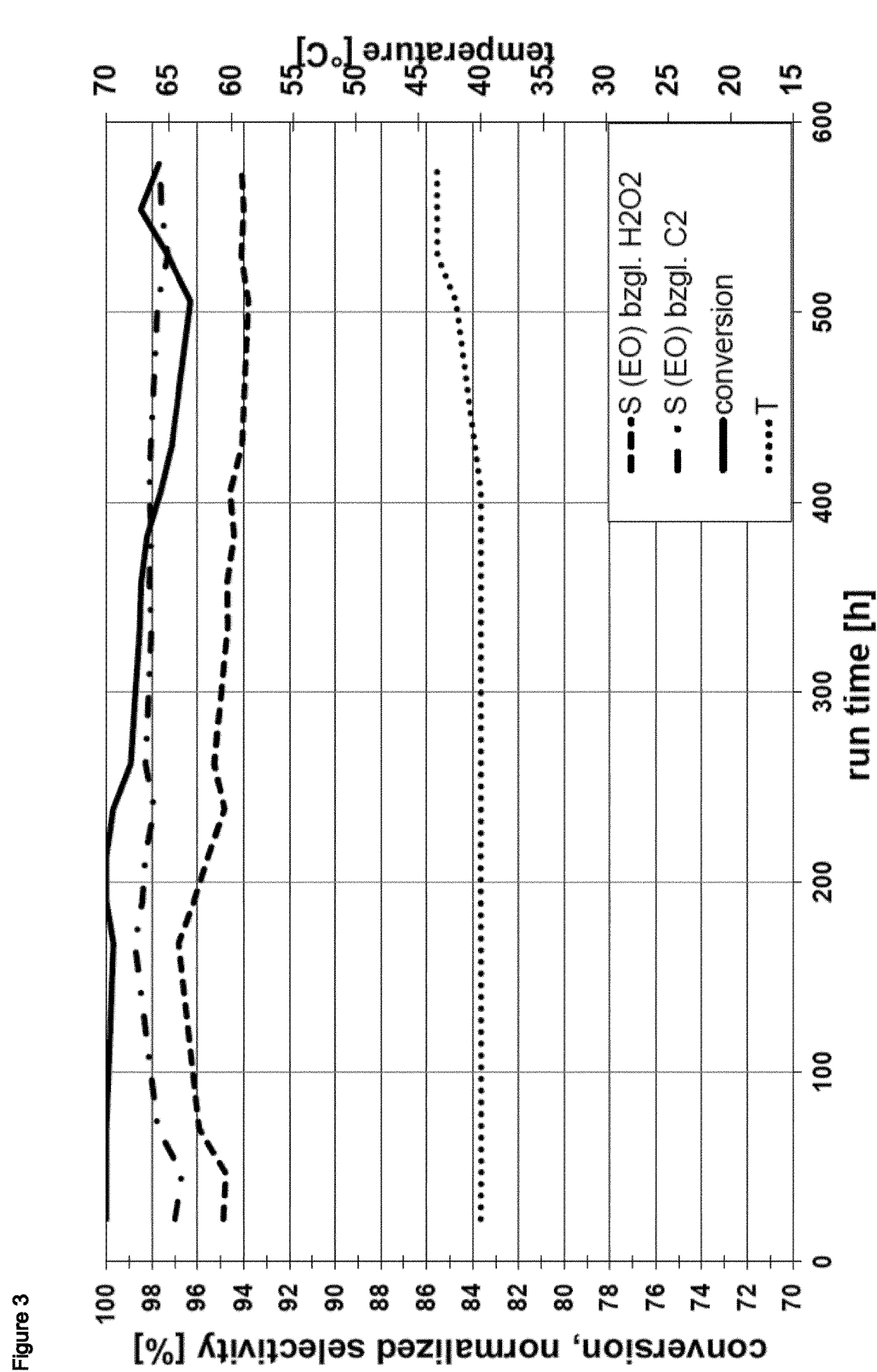
FIG. 3 shows the selectivities of ethene oxide during the first 600 hours time on stream of the epoxidation reaction as described in Example 2. The left hand Y axis shows the conversion of hydrogen peroxide in % and the normalized selectivities of ethene oxide based on hydrogen peroxide and based on ethene, respectively, both in %. The right hand Y axis shows the temperature in ° C. Further reference is made to the legend in FIG. 3.

US 20070099299 A1
Stallmach et al., in: Annual Reports on NMR Spectroscopy 2007, Vol. 61, pp. 51-131
X. Lu et al., Selective Synthesis of ethylene oxide through liquid-phase epoxidation of ethylene with titanosilicate/$H_2O_2$ catalytic systems, Applied Catalysis A: General, 515 (2016) 51-59
EP 1 122 249 A1
WO 2013/117536 A1

The invention claimed is:
1. A process for preparing ethene oxide, comprising:
(i) providing a liquid feed stream comprising ethene, hydrogen peroxide, and a solvent;
(ii) passing the liquid feed stream provided in (i) into an epoxidation zone comprising a catalyst comprising a titanium zeolite comprising zinc and having framework type MWW, subjecting the liquid feed stream to epoxidation reaction conditions in the epoxidation zone, and obtaining a reaction mixture comprising ethene oxide, water, and the solvent;
(iii) removing an effluent stream from the epoxidation zone, the effluent stream comprising ethene oxide, water, and the solvent.

2. The process of claim 1, wherein (i), (ii), and (iii) are each performed continuously.

3. The process of claim 1, wherein in the liquid feed stream provided in (i), a molar ratio of ethene relative to hydrogen peroxide is in a range of from 1:1 to 5:1.

4. The process of claim 1, wherein the solvent comprises one or more organic solvents.

5. The process of claim 1, wherein the liquid feed stream provided in (i) further comprises a dissolved salt.

6. The process of claim 1, wherein in the epoxidation zone according to (ii), the reaction mixture is liquid under the epoxidation conditions.

7. The process of claim 1, wherein the epoxidation zone according to (ii) comprises a first epoxidation subzone consisting of one or more epoxidation reactors A,
wherein, if the first epoxidation subzone comprises two or more epoxidation reactors A, the two or more epoxidation reactors A are arranged in parallel, and
wherein in (ii), the liquid feed stream provided in (i) is passed into at least one of the epoxidation reactors A, wherein the epoxidation conditions according to (ii) comprise:
an epoxidation temperature in the first epoxidation subzone in a range of from 20 to 60° C., wherein the epoxidation temperature is defined as the temperature of a heat transfer medium used for adjusting a temperature of the reaction mixture in the first epoxidation reaction subzone, and
a first epoxidation reaction pressure in a range of from 18 to 60 bar(abs), wherein the first epoxidation reaction pressure is defined as an absolute pressure at an exit of the first epoxidation subzone.

8. The process of claim 7, wherein the epoxidation conditions according to (ii) comprise a catalyst loading in the first epoxidation subzone in a range of from 0.05 to 125 $h^{-1}$,
wherein the catalyst loading is defined as a ratio of a mass flow rate in kg/h of hydrogen peroxide comprised in the liquid feed stream provided in (i) relative to an amount in kg of the catalyst comprising a titanium zeolite comprising zinc and having framework type MWW comprised in the first epoxidation subzone according to (ii).

9. The process of claim 1, wherein the titanium zeolite comprising zinc and having framework type MWW comprised in the catalyst according to (ii) comprises:
titanium, calculated as elemental titanium, in an amount in a range of from 0.1 to 5 weight-%, based on a total weight of the titanium zeolite comprising zinc and having framework type MWW, and
zinc, calculated as elemental zinc, in an amount in a range of from 0.1 to 5 weight-%, based on the total weight of the titanium zeolite comprising zinc and having framework type MWW,
wherein at least 98 weight-% of the titanium zeolite comprising zinc and having framework type MWW consists of Zn, Ti, Si, O, and H.

10. The process of claim 1, wherein the catalyst comprising the titanium zeolite comprising zinc and having framework type MWW is in the form of a molding comprising:
the titanium zeolite comprising zinc and having framework type MWW and
a binder.

11. The process of claim 1, wherein the epoxidation conditions according to (ii) comprise a hydrogen peroxide conversion in a range of from 85 to 100%,
wherein the hydrogen peroxide conversion is defined as $100 \times (1-y)$ %, wherein y is a molar amount of hydrogen peroxide comprised in the effluent stream removed in (iii) relative to a molar amount of hydrogen peroxide comprised in the liquid feed stream provided in (i).

12. The process of claim 1, wherein the effluent stream removed in (iii) comprises ethene oxide, water, the solvent, ethene, and oxygen, the process further comprising:
(iv) separating ethene and oxygen from the effluent stream, and obtaining:
a stream S1 which, relative to the effluent stream, is enriched in ethene oxide, the solvent, and water; and
a stream which, relative to the effluent stream, is enriched in ethene and oxygen.

13. The process of claim 12, further comprising:
(iv-2) reducing an oxygen content of the stream enriched in ethene and oxygen, and obtaining a stream comprising ethene and depleted in oxygen relative to the stream enriched in ethene and oxygen;
wherein the stream comprising ethene and depleted in oxygen is recycled, optionally after one or more work-up stages, to (i).

14. The process of claim 12, further comprising:
(v) separating ethene oxide from the stream S1, obtaining a stream S11 comprising ethene oxide and depleted of the solvent and water relative to the stream S1, and obtaining a stream S12 enriched in the solvent and water relative to the stream S1;
wherein the stream S12 enriched in the solvent and water is recycled, optionally after one or more work-up stages, to (i).

15. The process of claim 14, further comprising:
(v-2) subjecting the stream S11 comprising ethene oxide and depleted of the solvent and water to further purification with regard to ethene oxide.

* * * * *

UNITED STATES PATENT AND TRADEMARK OFFICE
CERTIFICATE OF CORRECTION

PATENT NO. : 10,774,057 B2
APPLICATION NO. : 16/310645
DATED : September 15, 2020
INVENTOR(S) : Parvulescu et al.

Page 1 of 2

It is certified that error appears in the above-identified patent and that said Letters Patent is hereby corrected as shown below:

On the Title Page

In Column 1, item (54), Line 1, "PROCESS" should read -- A PROCESS --.

In Column 1, item (51), under "Int. Cl.", Lines 1-2,
"*C07D 301/12*  (2006.01)
*B01J 29/70*     (2006.01)" should read -- *C07D 301/12*  (2006.01) --.

In the Specification

In Column 1, Line 1, "PROCESS" should read -- A PROCESS --.

In Column 2, Line 30, "methylacetate," should read -- methyl acetate, --.

In Column 5, Line 2, "weight %" should read -- weight-% --.

In Column 8, Line 40, "from from" should read -- from --.

In Column 9, Line 7, "spraypowder," should read -- spray-powder, --.

In Column 10, Line 46, "spray powder," should read -- spray-powder, --.

In Column 12, Line 53, "completey" should read -- completely --.

In Column 12, Line 62, "oxygen" should read -- oxygen. --.

In Column 15, Line 30, "methylacetate," should read -- methyl acetate, --.

In Column 20, Line 39, "a a" should read -- a --.

Signed and Sealed this
Ninth Day of March, 2021

Drew Hirshfeld
*Performing the Functions and Duties of the
Under Secretary of Commerce for Intellectual Property and
Director of the United States Patent and Trademark Office*

In Column 20, Line 47, "salt and." should read -- salt. --.

In Column 20, Line 65, "acetate" should read -- acetate. --.

In Column 25, Line 33, "H2O2" should read -- $H_2O_2$ --.

In Column 25, Line 34, "H2O2" should read -- $H_2O_2$ --.

In Column 25, Line 60, "CO2" should read -- $CO_2$ --.

In the Claims

In Column 27, Claim 8, Line 43, "125" should read -- 1.25 --.

In Column 28, Claim 10, Line 15, "MWW" should read -- MWW, --.